(12) United States Patent
Peeters et al.

(10) Patent No.: US 10,918,511 B2
(45) Date of Patent: Feb. 16, 2021

(54) INGESTIBLE INTRAGASTRIC BALLOON

(71) Applicant: Verily Life Sciences LLC, South San Francisco, CA (US)

(72) Inventors: Eric Peeters, Redwood City, CA (US); Peter Smith, Pacifica, CA (US); Benjamin Krasnow, Redwood City, CA (US); Peter Massaro, San Carlos, CA (US)

(73) Assignee: VERILY LIFE SCIENCES LLC, South San Francisco, CA (US)

( * ) Notice: Subject to any disclaimer, the term of this patent is extended or adjusted under 35 U.S.C. 154(b) by 303 days.

(21) Appl. No.: 16/036,005

(22) Filed: Jul. 16, 2018

(65) Prior Publication Data

US 2019/0029857 A1 Jan. 31, 2019

Related U.S. Application Data

(60) Provisional application No. 62/537,272, filed on Jul. 26, 2017.

(51) Int. Cl.
*A61F 5/00* (2006.01)

(52) U.S. Cl.
CPC ............ *A61F 5/003* (2013.01); *A61F 5/0036* (2013.01); *A61F 5/0046* (2013.01);
(Continued)

(58) Field of Classification Search
CPC ....... A61F 5/003; A61F 5/0036; A61F 5/0073
See application file for complete search history.

(56) References Cited

U.S. PATENT DOCUMENTS 3,797,492 A * 3/1974 Place ................... A61K 9/0004
604/890.1
6,579,301 B1 6/2003 Bales et al.
(Continued)

FOREIGN PATENT DOCUMENTS

EP 0103481 3/1984
JP 2007200739 8/2007
(Continued)

OTHER PUBLICATIONS

PCT/US2018/042288 , "International Preliminary Report on Patentability", dated Feb. 6, 2020, 9 pages.
(Continued)

*Primary Examiner* — Gregory A Anderson
(74) *Attorney, Agent, or Firm* — Kilpatrick Townsend & Stockton LLP

(57) ABSTRACT

An intragastric balloon device including a deformable material is in an ingestible form for delivery to a stomach of a patient, expands in response to stimuli in the stomach, and degrades within a limited duration (such as 16 hours or some other value between 2 hours and 72 hours) to diminish to passable form in which remains of the intragastric balloon device are passable from the stomach. In an illustrative example, the deformable material is composed of silicone coated with parylene and encloses perfluoropentane fluid that transitions from liquid to gas due to stomach temperature to inflate the balloon in the stomach and occupy space in the stomach until a fuse of methacrylate erodes to unblock a vent conduit to permit escape of the perfluoropentane for deflating the balloon to diminish to passable form.

32 Claims, 5 Drawing Sheets

(52) U.S. Cl.
CPC ...... *A61F 5/0073* (2013.01); *A61F 2005/002* (2013.01); *A61M 2210/1053* (2013.01)

(56) References Cited

U.S. PATENT DOCUMENTS

| | | | |
|---|---|---|---|
| 2004/0186502 A1* | 9/2004 | Sampson | A61F 5/0036 |
| | | | 606/191 |
| 2006/0058829 A1 | 3/2006 | Sampson et al. | |
| 2007/0104754 A1 | 5/2007 | Sterling et al. | |
| 2007/0104755 A1* | 5/2007 | Sterling | A61F 2/04 |
| | | | 424/423 |
| 2007/0135829 A1* | 6/2007 | Paganon | A61F 5/0036 |
| | | | 606/192 |
| 2008/0107732 A1 | 5/2008 | Dharmadhikari et al. | |
| 2010/0022836 A1* | 1/2010 | Colliou | H01Q 1/273 |
| | | | 600/118 |
| 2010/0222642 A1 | 9/2010 | Trovato | |
| 2012/0296365 A1 | 11/2012 | Nguyen | |
| 2013/0218190 A1 | 8/2013 | Gaur et al. | |

FOREIGN PATENT DOCUMENTS

| | | |
|---|---|---|
| WO | 2006020929 | 2/2006 |
| WO | 2016145076 | 9/2016 |
| WO | 2016200612 | 12/2016 |

OTHER PUBLICATIONS

PCT/US2018/042288 , "International Search Report and Written Opinion", dated Oct. 8, 2018, 15 pages.

* cited by examiner

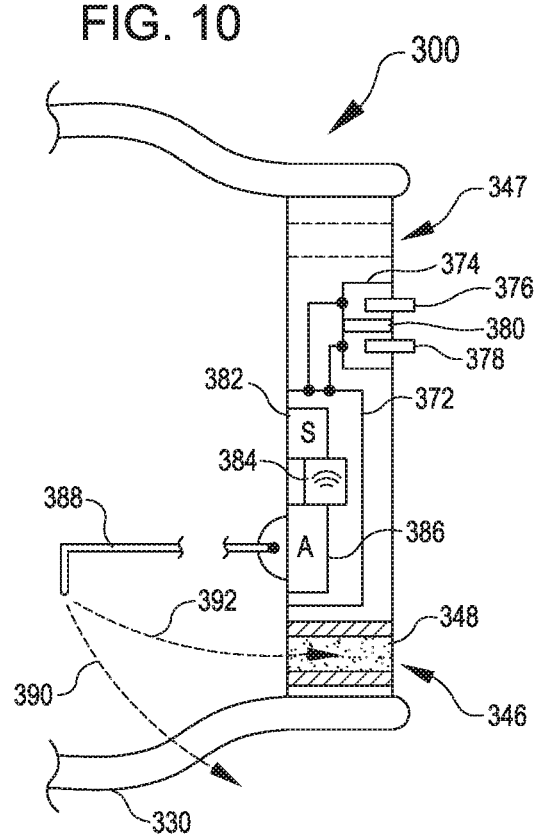

INGESTIBLE INTRAGASTRIC BALLOON

CROSS-REFERENCE TO RELATED APPLICATION

This application claims the benefit of U.S. Application No. 62/537,272, filed Jul. 26, 2017, titled "Ingestible Intragastric Balloon," which is incorporated herein by reference in its entirety.

TECHNICAL FIELD

The present disclosure generally relates to devices for suppressing appetite or increasing a sensation of satiety and their uses, and more specifically, but not necessarily limited to, intragastric balloon devices that are ingestible for delivery to the stomach.

BACKGROUND

One current intervention for treating obesity is installing saline-filled balloons in the stomach of a patient. These balloons occupy stomach volume, reducing the space available for food. These balloons are typically installed in an endoscopic surgical procedure and are removed via another endoscopic procedure.

SUMMARY

Various examples of the present disclosure are directed to intragastric balloon devices deliverable to the stomach by ingestion (e.g., rather than via endoscopic procedures).

In one example, an intragastric balloon device includes a deformable material. The balloon device is in an ingestible form for delivery to a stomach of a patient, expands in response to stimuli in the stomach, and degrades within 72 hours (or other suitable time range) to diminish to passable form in which remains of the intragastric balloon device are passable from the stomach.

In another example, a method of fabricating an ingestible intragastric balloon device is provided. The method can include providing a balloon including a deformable material forming a boundary between an interior volume within the balloon and an exterior outside of the balloon. The method can further include introducing an amount of liquid into the interior volume of the balloon, where the amount is selected to be sufficient to cause the balloon to inflate as the amount converts from liquid to gas as a temperature of the amount rises in response to the balloon being located within a stomach of a patient. The method can further include securing a fuse in a position blocking fluid flow through a vent conduit arranged with an interior-facing end in fluid communication with the interior volume and an exterior-facing end in fluid communication with the exterior. Characteristics of the fuse can be selected to cause the fuse to erode in stomach conditions within 72 hours (or other suitable time range) to a degree that permits fluid passage through the vent conduit to deflate the balloon and facilitate passing of the balloon from the stomach.

In a further example, an intragastric balloon device includes a balloon, perfluoropentane liquid, a vent, and a fuse. The balloon includes a deformable material forming a boundary between an interior volume within the balloon and an exterior outside of the balloon. The perfluoropentane liquid is disposed within the interior volume of the balloon and present in a sufficient amount to cause the balloon to inflate toward a predetermined size as the amount of perfluoropentane converts from liquid to gas as a temperature of the perfluoropentane rises in response to the balloon being located within a stomach of a patient. The vent conduit has an interior-facing end in fluid communication with the interior volume and an exterior-facing end in communication with the exterior. The fuse includes methacrylate and is disposed blocking fluid flow through the vent conduit. The fuse sized and shaped to erode in stomach conditions within 2-72 hours (or other suitable time range) to a degree that permits fluid passage of the perfluoropentane through the vent conduit to deflate the balloon and facilitate passing of the balloon from the stomach.

In yet another example, a method of suppressing appetite in a subject can be provided. The method can include administering to the subject an intragastric balloon device, such as one described above.

These illustrative examples are mentioned not to limit or define the scope of this disclosure, but rather to provide examples to aid understanding thereof. Illustrative examples are discussed in the Detailed Description, which provides further description. Advantages offered by various examples may be further understood by examining this specification.

BRIEF DESCRIPTION OF THE DRAWINGS

The accompanying drawings, which are incorporated into and constitute a part of this specification, illustrate one or more certain examples and, together with the description of the example, serve to explain the principles and implementations of the certain examples.

FIG. 10 shows a side cutaway view of a plug with electrical components that may be utilized in conjunction an intragastric balloon device according to certain examples of the present disclosure.

DETAILED DESCRIPTION

Examples are described herein in the context of intragastric balloon devices. Those of ordinary skill in the art will realize that the following description is illustrative only and is not intended to be in any way limiting. Reference will now be made in detail to implementations of examples as illustrated in the accompanying drawings. The same reference indicators will be used throughout the drawings and the following description to refer to the same or like items.

In the interest of clarity, not all of the routine features of the examples described herein are shown and described. It will, of course, be appreciated that in the development of any such actual implementation, numerous implementation-specific decisions must be made in order to achieve the developer's specific goals, such as compliance with application- and business-related constraints, and that these specific goals will vary from one implementation to another and from one developer to another.

In an illustrative example, an obesity treatment program seeks to decrease hunger or increase sensations of satiety (e.g., a feeling of "fullness") to help control or reduce a patient's body weight. To do so, the treatment program provides a series of pills to the patient. Each pill includes a balloon that inflates toward a predetermined size in the stomach to occupy stomach volume and help the patient to feel full, thereby curbing additional food consumption and an associated risk of weight gain. Specifically, the balloon contains a liquid that has a vaporization point that is less than human body temperature. Thus, when the balloon reaches the stomach, the liquid is heated toward the body temperature and boils to change from liquid to gas and inflate the balloon. The balloon also is sealed with a plug that includes a fuse that will erode at a predictable rate when exposed to stomach acid. When the fuse is fully eroded, a path is left behind in the plug where the fuse was and allows the gas in the balloon to escape so that the balloon deflates. Thus, if the fuse is set, for example, to erode after 16 hours, the patient can take the pill first thing in the morning, have the balloon present in an inflated state all day to suppress hunger, and have the balloon deflate about the time the patient is going to bed (e.g., so that the patient can sleep without the balloon applying pressure in the stomach). Once the balloon is deflated, it is processed by the digestive system to pass out of the stomach (e.g., either whole or in pieces digested or partially digested by stomach acid, peristalsis, etc.). Thus, the balloon may be introduced, inflated, deflated, and removed without surgical intervention and in a manner much less invasive than surgical intervention.

Figure 1:
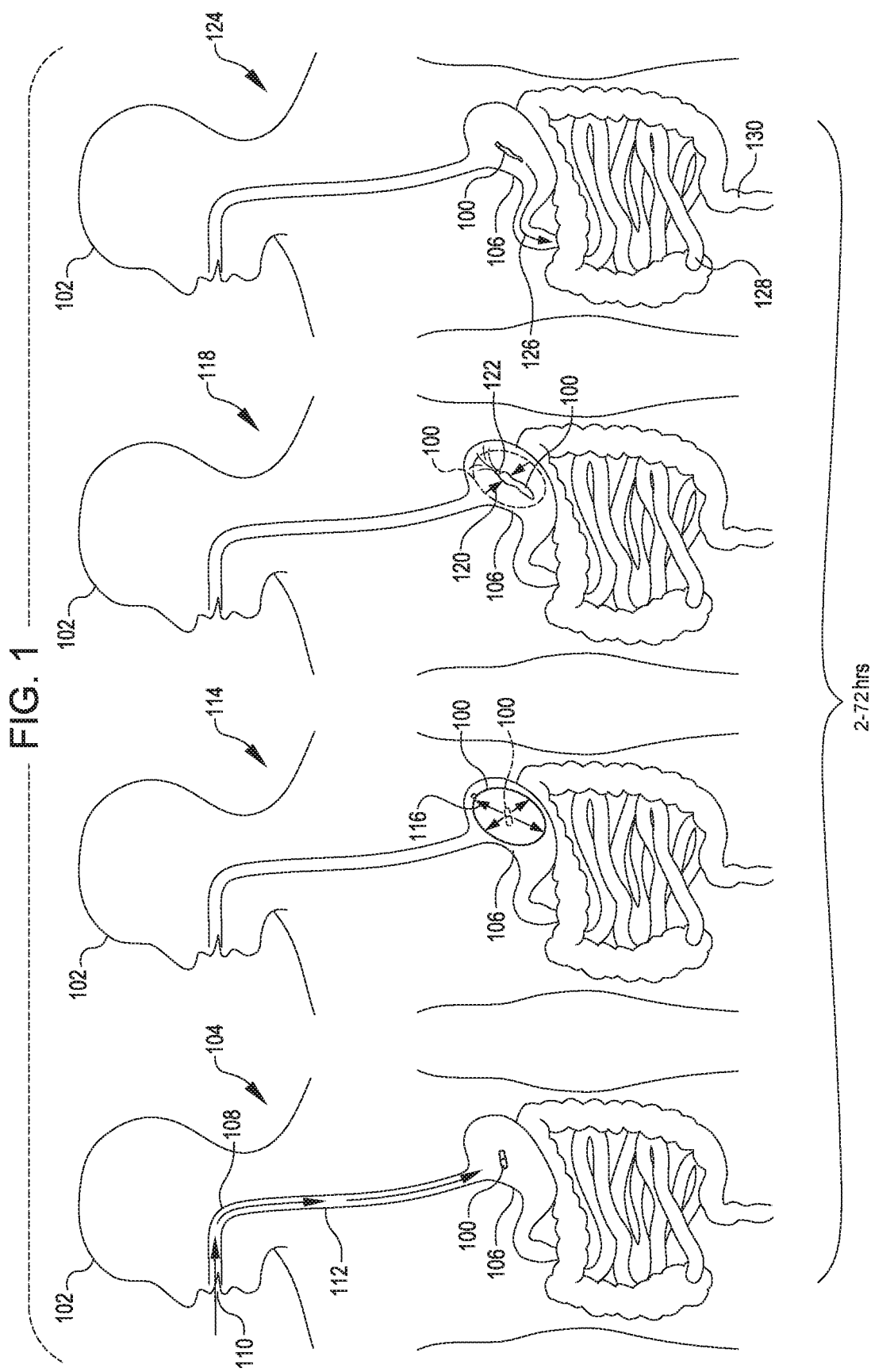
FIG. 1 illustrates an example progression of an intragastric balloon device in use relative to a patient according to certain examples of the present disclosure.

FIG. 1 illustrates an example progression of an intragastric balloon device 100 in use relative to a patient 102. At 104, the intragastric balloon device 100 is introduced into the patient's stomach 106. For example, the intragastric balloon device 100 can be contained in a pill or otherwise in an ingestible form that permits the intragastric balloon device 100 to be swallowed to pass (e.g., as depicted by arrows 108) through the patient's mouth 110 and esophagus 112 into the patient's stomach 106.

At 114, the intragastric balloon device 100 expands in the stomach 106 (e.g., as depicted by arrows 116), such as changing in size from the shape shown in phantom lines to the shape shown in solid lines at 114. The intragastric balloon device 100 expands in response to temperature or other stimuli in the stomach 106. While the intragastric balloon device 100 remains in the inflated state, it occupies space in the stomach 106 and causes the neurological system of the patient 102 to trigger signals associated with the stomach 106 being occupied. For example, as a result of the intragastric balloon device 100 being in the inflated state in the stomach 106, the patient 102 may experience a sensation of being full or satiety that may reduce an inclination of the patient 102 to eat, which in turn can assist the patient 102 in weight control efforts.

At 118, after a suitable amount of time, the intragastric balloon device 100 can deflate (e.g., as depicted by arrows 120), such as changing in size from the shape shown in phantom lines to the shape shown in solid lines at 118. The intragastric balloon device 100 deflates in response to gas or other fluid venting out of the intragastric balloon device 100 through a vent conduit 122. The vent conduit 122 can be formed or unblocked to allow venting in response to degradation or dissolution of a portion of the intragastric balloon device 100. For example, a portion of the intragastric balloon device 100 can erode over time in response to contact with stomach acid.

At 124, based at least in part on deflation, the intragastric balloon device 100 diminishes to a passable form in which remains of the intragastric balloon device 100 are passable from the stomach 106 (e.g., as depicted by arrow 126). For example, remains of the intragastric balloon device 100 may be passed out through the small intestine 128 and large intestine or colon 130 of the patient 102 within other excrement.

The intragastric balloon device 100 can be constructed with components selected to cause the intragastric balloon device 100 to last a suitable or desired limited duration between introduction into the stomach 106 (e.g., as at 104) and diminishing to passable form (e.g., as at 124). Causing the intragastric balloon device 100 to last a limited duration can have various effects that may address, resolve, or eliminate problems that may be encountered with implants that may be left in the stomach 106 for months on end or other extended durations.

Volume-occupying implants are typically left in the stomach 106 for months on end or other extended durations for a variety of reasons. Such implants are typically installed via endoscopic or other surgical procedures. The invasive nature of these procedures often requires an amount of recovery time that weighs against performing such procedures any more often than every few months. Moreover, the cost of performing such procedures is typically high, leading to a desire to maximize the amount of time that the effect of the procedure will last. Additionally, weight loss from a reduced appetite or reduced food intake is typically not a rapid process, so following the installation of such implants, a targeted amount of weight loss is typically only recorded following a corresponding extended duration of time with the implants present within the stomach 106.

Various issues can arise, however, with such extended-duration implants. In some cases, the sudden introduction of a sizable implant in the stomach 106 can press against portions of the stomach 106 or otherwise cause discomfort for the patient 102. Additionally, in some cases, the stomach 106 of the patient 102 may respond to the ongoing presence of an extended-duration implant by stretching or otherwise expanding to accommodate the implant. Long-term stretching of the stomach 106 may add space in the stomach 106 that offsets space occupied by the implant such that the effectiveness of the implant for appetite control or weight control is reduced or eliminated.

In contrast to extended-duration implants, in some examples, the intragastric balloon devices 100 may last a limited duration and permit the stomach 106 to relax between uses of successive intragastric balloon devices 100.

Such periodic relaxation may reduce or eliminate a risk that the stomach 106 will be subject to long-term stretching. Additionally, in some examples, the intragastric balloon device 100 lasting a limited duration can facilitate the gradual sequential introduction of successively larger intragastric balloon devices 100, e.g., which may mitigate against discomfort that in contrast could be experienced from instead having a full-size implant suddenly introduced and maintained for an extended duration. For example, a patient 102 progressing through a treatment regimen that includes successive short durations of small-size, medium-size, and large-size intragastric balloon devices 100 may have an opportunity to progressively become accustomed to the sensation of having something in the stomach 106 and avoid discomfort that might otherwise be experienced from having a large-size object introduced suddenly without previous opportunity to acclimate.

FIG. 1 by way of example indicates a range of between 2 hours and 72 hours for limited durations between introduction into the stomach 106 (e.g., as at 104) and diminishing to passable form (e.g., as at 124). Although various examples of respective duration amounts within this range will now be described, durations of the intragastric balloon devices 100 may additionally or alternatively be associated with other amounts and/or ranges, including, but not limited to, months on end or other amounts outside of the range of 2-72 hours or other ranges specifically described herein, and/or ranges between distinct amounts specifically referenced or not specifically referenced herein. Moreover, particular uses or benefits described as applicable for particular values additionally or alternatively may be applicable for other values too.

An intragastric balloon device 100 that diminishes to passable form in less than 2 hours may be useful for staging up between sizes of intragastric balloon devices 100. For example, such a duration may allow a patient 102 over the course of ten hours to have five successive 2-hour intervals that would each allow the patient 102 to have 2 hours to acclimate to a given size of intragastric balloon device 100 before moving on to the next size up, e.g., introducing a new, larger intragastric balloon device 100 each time an earlier intragastric balloon device 100 finished diminishing. Additionally or alternatively, an intragastric balloon device 100 that diminishes to passable form in less than 2 hours may be useful as a brief intervention to assist a patient 102 to curb appetite until a scheduled meal or snack time, e.g., if the patient were to ingest the intragastric balloon device 100 at 3 p.m. in anticipation for a next meal at 5 p.m. or at 8 a.m. in anticipation of a next snack at 10 a.m.

An intragastric balloon device 100 that diminishes to passable form in less than 4 hours may be useful as an intervention to assist a patient 102 to curb appetite between successive meals that are spaced a shorter distance apart. For example, a patient could ingest the intragastric balloon device 100 following an 8 a.m. breakfast in anticipation for a lunch at 12 p.m.

An intragastric balloon device 100 that diminishes to passable form in less than 6 hours may be useful as an intervention to assist a patient 102 to curb appetite between successive meals that are spaced a longer distance apart. For example, a patient could ingest the intragastric balloon device 100 following a 12 p.m. lunch in anticipation for a 6 p.m. dinner.

An intragastric balloon device 100 that diminishes to passable form in less than 8 hours may be useful as an intervention to assist a patient 102 to curb appetite, e.g., during a work day. For example, a patient could ingest the intragastric balloon device 100 at 9 a.m. to reduce appetite until a work day ends at 5 p.m. to reduce appetite for treats or large lunches that may be prominent or common fare in a workplace.

An intragastric balloon device 100 that diminishes to passable form in less than 12 hours may be useful as an intervention to assist a patient 102 to have equal amounts of time with the stomach 106 affected by the intragastric balloon device 100 and resting without the effect of the intragastric balloon device 100. For example, a patient could ingest the intragastric balloon device 100 when waking up at 7 a.m. in the morning, have the benefit of the intragastric balloon device 100 until 7 pm, and then have from 7 p.m. to 7 a.m. the following morning for the stomach 106 to be relaxed before a next intragastric balloon device 100 is ingested.

An intragastric balloon device 100 that diminishes to passable form in less than 16 hours may be useful as an intervention to assist a patient 102 to curb appetite throughout waking hours. For example, a patient could ingest the intragastric balloon device 100 when waking up at 7 a.m. in the morning and have the benefit of the intragastric balloon device 100 until going to bed at 11 pm, and then have from 11 p.m. to 7 a.m. the following morning for the stomach 106 to be relaxed while the patient 102 is sleeping and before a next intragastric balloon device 100 is ingested.

An intragastric balloon device 100 that diminishes to passable form in less than 24 hours may be useful as an intervention to assist a patient 102 to curb appetite through a regular daily cycle. For example, a patient could ingest the intragastric balloon device 100 when waking up one morning at 7 a.m. in the morning and have the benefit of the intragastric balloon device 100 until 7 a.m. the following morning, at which point the patient 102 might decide if the aid of another intragastric balloon device 100 is desired for the next 24 hours or if some other combination of durations is desired to allow the stomach 106 to rest in the interim. In a further illustrative example, the patient 102 could follow a "one day on, one day off" schedule.

An intragastric balloon device 100 that diminishes to passable form in less than 36 hours may be useful as an intervention to assist a patient 102 to curb appetite with less than daily rest periods for the stomach 106. For example, a patient 102 could ingest the intragastric balloon device 100 when waking up one morning (e.g., Monday) at 7 a.m. in the morning, have the benefit of the intragastric balloon device 100 until 7 p.m. the following evening (e.g., Tuesday), and then have from 7 p.m. to 7 a.m. the subsequent morning (e.g., Wednesday) for the stomach 106 to be relaxed before a next intragastric balloon device 100 is ingested. Such a duration may permit the patient to follow a "one night on, one night off" schedule.

An intragastric balloon device 100 that diminishes to passable form in less than 72 hours may be useful as an intervention to assist a patient 102 to curb appetite with rest periods for the stomach 106 separated by multiple days. For example, a patient 102 could ingest the intragastric balloon device 100 when waking up one morning (e.g., Monday) at 7 a.m. in the morning, have the benefit of the intragastric balloon device 100 until 7 a.m. three days later (e.g., Thursday), and then have until a later time such as 7 a.m. the subsequent morning (e.g., Friday) for the stomach 106 to be relaxed before a next intragastric balloon device 100 is ingested. Such a duration may permit the patient to follow a "multiple days on, and lesser time off" schedule.

Other treatment plans are also possible. For example, an intragastric balloon device 100 that diminishes to passable form in less than 40 hours may be a useful duration corresponding to a full 24 hour period plus a 16 hour period of waking hours that may allow a patient 102 to have the intragastric balloon device 100 in use for all of the waking hours over a two day span while allowing the stomach 106 to rest every other night. Additionally or alternatively, in some examples, a treatment plan may include a patient 102 having more than one intragastric balloon device 100 in the stomach 106 at one time. For example, a target volume to occupy within the stomach 106 may be achieved by introducing a set of intragastric balloon devices 100 that each are sized to occupy a subset or fraction of the target volume but collectively when combined together occupy the whole target volume. Providing relatively smaller intragastric balloon devices 100 may accordingly permit customization per patient 102, for example, allowing different patients 102 to ingest different numbers of the intragastric balloon devices 100 to accommodate differences in physiology or intervention intensity. For convenience, the intragastric balloons may be provided in a kit that includes multiple intragastric balloons suitable for all or a portion of the subject's treatment period.

Thus, provided herein are methods of suppressing appetite in a subject in need of such suppression. These methods include administering to the subject an intragastric balloon as described herein. The subject, for example, may be obese or otherwise be in need of weight loss or control. Optionally, the subject self-administered the intragastric balloon by swallowing it. Various treatment regimens can be utilized based, for example, on the age, weight, height, sex, and diagnosis of the subject. Treatment regimens may include administration of intragastric balloon daily to the subject but may also include less frequent administrations. Optionally the duration of the treatment period during which the intragastric balloons are administered regularly is at least 2 days to at least 3 months (for example for 1 week or 1 month), but could be longer. The treatment regimen may include administering intragastric balloons of different sizes. For example, the subject may be administered progressively larger sized intragastric balloons during the treatment period, for example, small balloons followed by medium or larger balloons. The period of successively larger balloons may be followed by a second period of successively smaller balloons. The duration and specific treatment regimen can be determined by one of skill in the art.

Figure 2:
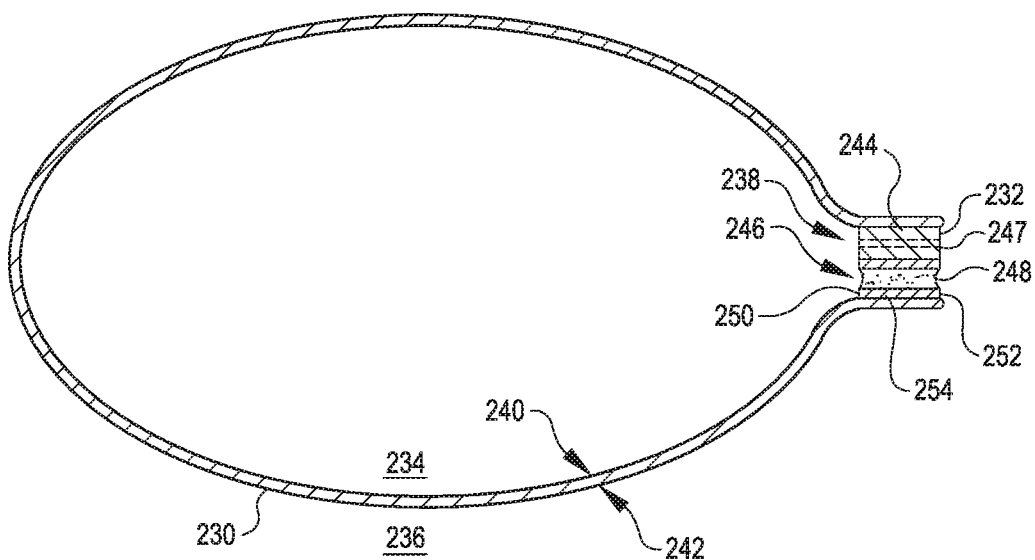
FIG. 2 is a side cutaway view illustrating parts of an example of an intragastric balloon device according to certain examples of the present disclosure.

FIG. 2 is a side cutaway view illustrating a construction of an example of an intragastric balloon device 200. The intragastric balloon device 200 is an example of the intragastric balloon device 100. The intragastric balloon device 200 is shown in an inflated state in FIG. 2. The intragastric balloon device 200 shown in FIG. 2 includes a balloon 230 and a plug 232.

The balloon 230 is formed from a deformable material. The deformable material defines a boundary between an interior volume 234 of the balloon 230 and an exterior 236 outside of the balloon 230. The deformable material of the balloon 230 also defines a mouth 238 that defines a transition passage between the interior volume 234 and the exterior 236 of the balloon 230. The deformable material also includes an inside surface 240 that faces the interior volume 234 of the balloon 230 and outside surface 242 that faces the exterior 236 outside of the balloon 230.

Various materials may be suitable for the deformable material of the balloon 230. Generally, the deformable material of the balloon 230 can include material that can expand or contract in response to expansion or contraction of the interior volume 234, such as by gas expansion in the interior volume 234. Non-limiting examples of the deformable material of the balloon 230 include silicone or biaxially-oriented polyethylene terephthalate. Moreover, various types of the balloon 230 may be utilized. One type may include a relatively highly stretchable material (e.g., rubbers) and inflate like a traditional balloon. Non-limiting examples of suitable material for such a first type of balloon 230 include rubber such as silicone or urethane or vinyl rubber or latex, or other known rubbers or comparable materials. Another type may include a relatively non-stretch (or low stretch) material, e.g., more akin to a plastic bag than a rubber balloon. For example, the balloon 230 may be rolled up inside the capsule and then unfurl and fill with gas, occupying a larger volume without substantial stretching the material of the balloon 230. Non-limiting examples of suitable material for such a second type of balloons 230 include plastic films such as polyethylene or polyimide or polyester, or other known plastic films or comparable materials. In some examples, such second type of balloon 230 may include non-polymeric materials including natural materials, e.g. natural sausage casing (intestines) or lamb skin etc.

In some examples, the deformable material of the balloon 230 can be treated with or include particular materials to enable certain functions for the balloon 230. For example, the balloon 230 can include a material that breaks down in high-pH environments (e.g., environments of the small intestine, which typically range in pH between 6 to 8). Such construction may allow the balloon 230 to break down once deflated and passed out of the stomach 106 into the small intestine and/or allow the balloon 230 to be chemically disrupted (ruptured) before deflation by the patient drinking baking soda water or otherwise introducing a high-pH-inducing fluid, such as in case of an emergency in which waiting for the balloon 230 to begin deflating automatically is not a viable option. Alternatively, the balloon 230 in some examples can be excreted by being transported whole through the intestines. In some examples, the deformable material of the balloon 230 can have a controlled permeability to provide an additional or alternative method for controlled deflation of the intragastric balloon device 200.

In some examples, the deformable material of the balloon 230 can be coated with parylene or other substances. For example, coating silicone with parylene, or other low permeability barrier films (e.g., with a thickness of 5 microns) may reduce permeability of the silicone while maintaining favorable elasticity characteristics of the silicone.

The inside surface 240 and the outside surface 242 of the balloon 230 can be treated the same or differently. In one example, both the inside surface 240 and the outside surface 242 are treated with parylene to provide favorable characteristics of the balloon 230. In another example, the outside surface 242 is treated with parylene to provide favorable characteristics of the balloon 230 while the inside surface 240 includes material that breaks down in low-pH environments (e.g., environments of the stomach, which typically ranges in pH between 1 to 2.5) so that the balloon 230 can degrade from the inside out when penetrated to permit stomach acid into the interior volume 234.

The plug 232 shown in FIG. 2 is positioned in the mouth 238 of the balloon 230. The plug 232 can function to seal contents within the interior volume 234 of the balloon 230. The plug 232 can also include features for facilitating release of contents from out of the interior volume 234. The plug 232 shown in FIG. 2 includes a plug body 244, a vent conduit 246, a fill conduit 247, and a fuse 248. The plug body 244 can be formed of silicone or any other suitable material, e.g., which may include material approved for use in the human body by relevant government or other regulatory agencies.

The fill conduit 247 shown in FIG. 2 extends through the plug body 244. The fill conduit 247 may provide a passage for introducing fluid into the interior volume 234 of the balloon. The fill conduit 247 may be formed to receive a needle, for example, as described in greater detail below with respect to FIG. 3.

The vent conduit 246 includes an interior-facing end 250 and an exterior-facing end 252. In FIG. 2 (e.g., when the plug 232 is received in the mouth 238), the interior-facing end 250 of the vent conduit 246 is in fluid communication with the interior volume 234 and the exterior-facing end 252 of the vent conduit 246 is in fluid communication with the exterior 236. A tube 254 of steel, metal, plastic, or other rigid material is shown in FIG. 2 extending through the plug 232 to define the vent conduit 246, although other arrangements of the vent conduit 246 are possible. In some examples, the vent conduit 246 is formed as a hole through material of the plug body 244, e.g., without a separate tube 254 of metal or other material. In some examples, the vent conduit 246 can be formed in the balloon 230 or in other structure apart from the plug 232.

The fuse 248 can be positioned for blocking fluid flow through the vent conduit 246. In FIG. 2, the fuse 248 is positioned within the vent conduit 246. Additionally or alternatively, the fuse 248 may be positioned covering one or both of the interior-facing end 250 and the exterior-facing end 252 of the vent conduit 246. The position of the fuse 248 may be such that in the absence of the fuse 248 (e.g., following erosion of the fuse 248), fluid flow can pass through the vent conduit 246. The fuse 248 can make up all or part of the plug 232 to permit fluid flow through the mouth 238 of the balloon 230 in the absence of the fuse 248 (e.g., following erosion of the fuse 248).

The fuse 248 can have characteristics selected to cause the fuse 248 to erode in stomach conditions within a particular duration to a degree that permits fluid passage through the vent conduit 246 (e.g., to permit deflation of the balloon 230 to facilitate passing of the balloon 230 from the stomach 106). In various examples, the characteristics of the fuse 248 may be a principle factor in achieving the durations described above with respect to FIG. 1. Example characteristics of the fuse 248 that may affect a duration of the fuse 248 can include a composition of the fuse 248, a length of the fuse 248, and/or a cross-section or surface area of the fuse 248 that is exposed for contact with stomach conditions. As an illustrative example, reducing an overall length of the fuse 248 and/or increasing a size of an exposed cross-section of the fuse 248 can reduce an amount of time before the vent conduit 246 will be cleared in response to stomach acid to permit deflation.

The composition of the fuse 248 can include any material that can decay, dissolve, degrade, or otherwise erode at a predictable rate when exposed to conditions in the stomach 106. For example, the fuse 248 can include methacrylate material, e.g., butylated methacrylate copolymer, polymethacrylate, etc. In some examples, the methacrylate material may be cross-linked with a low-pH-soluble material so that the fuse 248 will erode in the stomach 106 in response to contact with stomach acid (e.g., having a pH below 2.5). Methacrylate material is typically used as a thin film coating to maintain integrity of capsules for pills swallowed by ingestion. The fuse 248 may be formed of similar material, but may differ in preparation from the thin film coating typically utilized for capsules and pills (e.g., so that the fuse 248 includes a greater concentration of methacrylate material than that typically used in coatings for capsules or pills). For example, whereas methacrylate material for pill coatings may be used in a liquid form for dipping capsules into, the methacrylate material for the fuse 248 may be produced as a solid or semi-solid mass.

FIGS. 3-9 illustrate examples of the intragastric balloon device 200 at various stages of fabrication and use.

Figure 3:
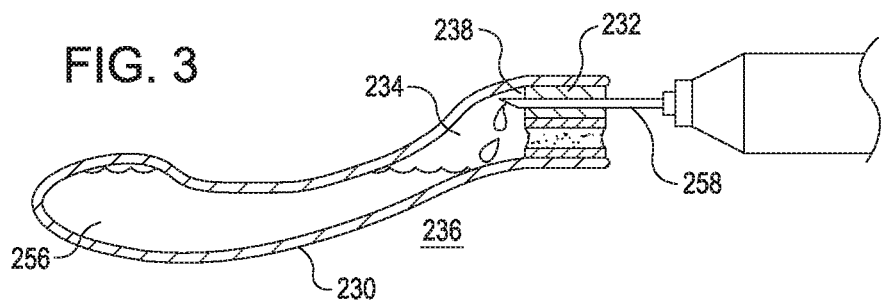
FIG. 3 is a side cutaway view of the intragastric balloon device of FIG. 2 with fluid introduced into the interior volume of the balloon device according to certain examples of the present disclosure.

Referring to FIG. 3, in fabricating the intragastric balloon device 200, the plug 232 is inserted and installed into the mouth 238 of the balloon 230, e.g. to seal the interior volume 234. The fuse 248 may be installed relative to the vent conduit 246 before or after installing the plug 232 in the mouth 238, with the end result being that the fuse 248 is secured in a position blocking fluid flow through the vent conduit 246 between the interior volume 234 of the balloon 230 and the exterior 236 of the balloon 230.

In FIG. 3, a needle 258 is inserted through the fill conduit 247 (FIG. 2) to provide a conduit for introducing fluid 256 into the interior volume 234 of the balloon 230. In some examples, the fill conduit 247 is defined by silicone or other material that can be pushed apart by the needle 258 as the needle 258 is inserted and can also flex back inwardly to form a seal as the needle 258 is extracted (e.g., similar to a septum). The fill conduit 247 may be formed by the action of puncturing via the needle 258 or may be pre-formed before insertion of the needle 258. The fill conduit 247 may be formed from the same material or a different material as the plug body 244 (FIG. 2). In some examples, after use of the fill conduit 247 to introduce fluid 256 into the interior volume 234, the fill conduit 247 can be filled with material (which may be of a same or different kind of material from the plug body 244) to seal and prevent fluid flow through the fill conduit 247. As an illustrative example, silicone may be injected into the fill conduit 247 for sealing after a suitable amount of the fluid 256 is introduced via the needle 258. Although FIG. 3 illustrates a needle 258 inserted through the fill conduit 247 for introducing the fluid 256, in some examples, the needle 258 and/or the fill conduit 247 may be omitted. For example, the fluid 256 may be introduced into the interior volume 234 prior to installing the plug 232 in the mouth 238 of the balloon 230 or via other methods.

The fluid 256 can correspond to any biocompatible fluid that has a vaporization point less than a body temperature of the patient 102 (e.g., less than a body temperature of the human body if the patient 102 is a human). This characteristic can allow the fluid to change from a liquid to a gas and thus expand to inflate the balloon 230 following introduction into the patient 102. One example of a suitable liquid for the fluid 256 is perfluoropentane. For example, perfluoropentane has a vaporization point near the human body temperature (e.g., begins to transition from liquid to gas between 30° C. and 35° C.) and has previously received FDA approval for use in the human body (e.g., for IV injection as a contrast agent). Moreover, perfluoropentane exhibits a significant volume expansion upon vaporization. For example, 1.0-1.5 mL of perfluoropentane in liquid form can expand to occupy 200-250 mL of volume in gas form.

Figure 4:
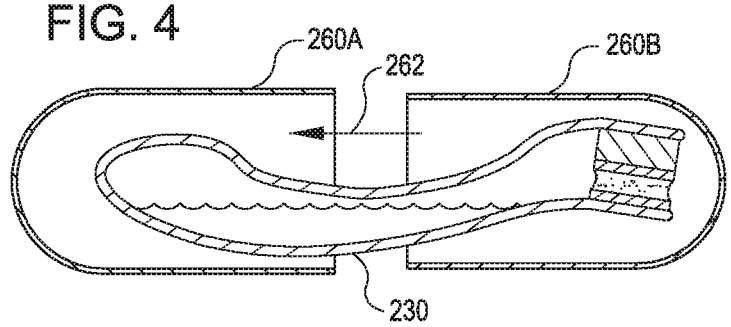
FIG. 4 is a side cutaway view of the intragastric balloon device of FIG. 2 partially received within capsule parts according to certain examples of the present disclosure.
Figure 5:
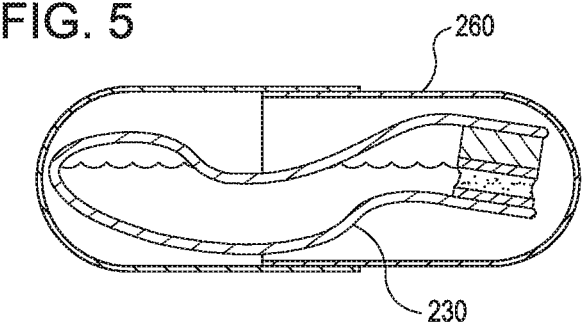
FIG. 5 is a side cutaway view of the intragastric balloon device of FIG. 2 contained within a pill formed by the capsule parts of FIG. 4 according to certain examples of the present disclosure.
Figure 6:
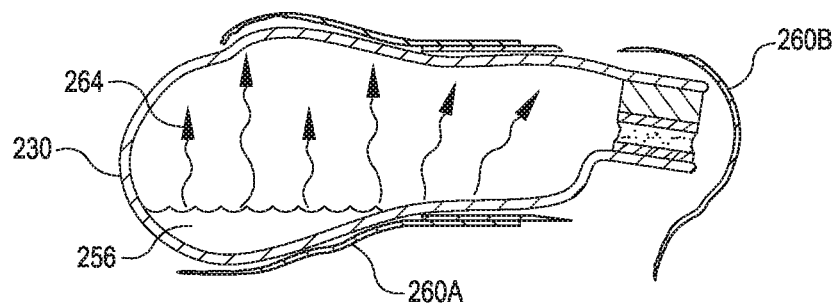
FIG. 6 is a side cutaway view of the intragastric balloon device of FIG. 2 in a partially inflated state within a stomach of a patient according to certain examples of the present disclosure.

Referring to FIG. 4, following preparation of the balloon 230 to include a suitable amount of liquid 256 sealed within the interior volume 234 of the balloon 230, capsule parts 260A and 260B can be assembled (e.g., as illustrated by arrow 262) about the balloon 230. Such assembly can result in the balloon 230 being enclosed in a capsule 260, e.g., as shown in FIG. 5. The capsule 260 can be a gelatin capsule or any other suitable coating for facilitating delivery by swallowing to the stomach 106 of a patient 102. The capsule 260 may correspond in size to a size of pill for human consumption by ingestion approved by the Food and Drug Administration ("FDA") or other regulatory body. In some examples, the capsule 260 can be coated in methacrylate (e.g., at a more dilute concentration than used for the fuse 248) or other suitable coating to maintain an integrity of the capsule until reaching the stomach 106 of the patient 102, or the capsule itself can be made of methacrylate. Referring to FIG. 6, following introduction of the capsule 260 into the stomach 106 of the patient 102, the capsule parts 260A and 260B can begin to dissolve, erode, or otherwise break apart. The liquid 256 within the balloon 230 can begin to evaporate (e.g. as illustrated by arrows 264) and form gas that can cause the balloon 230 to begin to inflate and expand. Expansion of the balloon 230 can act in conjunction with the degradation of the capsule parts 260a and 260B to cause the capsule 260 to break apart and leave the balloon 230 and associated components exposed to the environment within the stomach 106.

Figure 7:
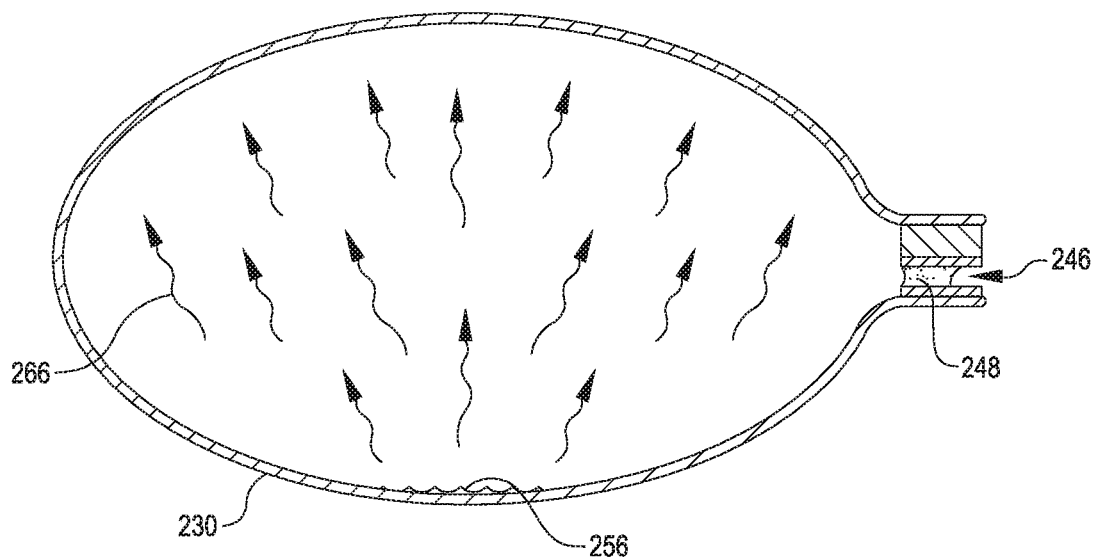
FIG. 7 is a side cutaway view of the intragastric balloon device of FIG. 2 in a fully inflated state with a portion of a fuse dissolved from exposure within the stomach of a patient according to certain examples of the present disclosure.

Referring to FIG. 7, the fluid 256 can continue to evaporate (e.g. as illustrated by arrows 266) from liquid into gas based on the temperatures within the stomach 106 being above the vaporization point of the fluid 256. As a result, the balloon 230 can inflate to its fully expanded size (e.g., expanding from the size shown in FIG. 6 to the size shown in FIG. 7). In some examples, the balloon 230 may inflate to its full size within 30 seconds to one minute. The balloon 230 can exhibit a sufficiently low permeability (e.g., due to the parylene coating on the balloon 230 if present) to retain the gas within the balloon 230 and maintain the balloon 230 in an inflated state. Furthermore, the stomach acid within the stomach 106 (that is no longer blocked by the capsule 260) can act on the fuse 248 and cause the fuse 248 to begin to erode (e.g., reducing in size from that shown in FIG. 6 to the size shown in FIG. 7). The duration that the fuse 248 lasts before permitting fluid flow through the vent conduit 246 can be determined based on characteristics of the fuse 248, such as described above with respect to FIG. 2.

Figure 8:
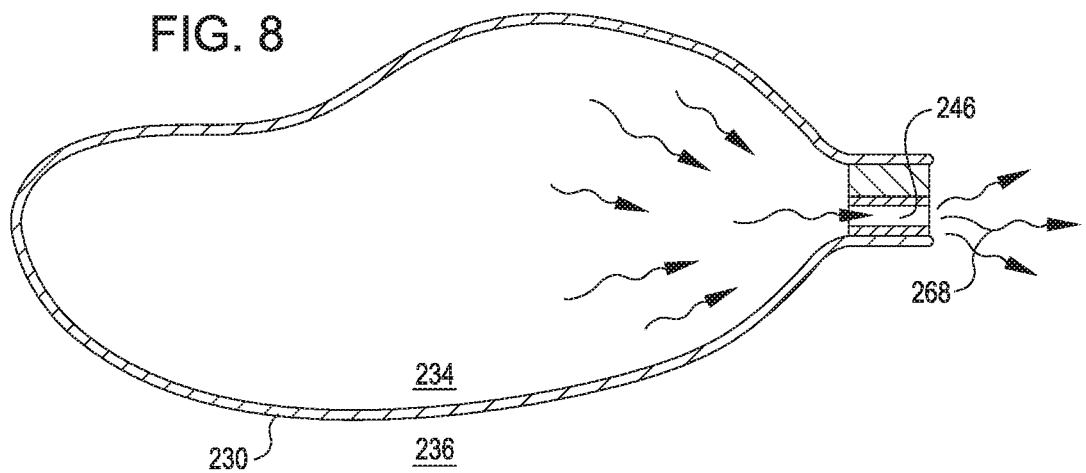
FIG. 8 is a side cutaway view of the intragastric balloon device of FIG. 2 in a partially deflated state in the absence of the fuse of FIG. 6 according to certain examples of the present disclosure.

Referring to FIG. 8, when the fuse 248 has sufficiently eroded to permit fluid flow through the vent conduit 246, the gas in the interior volume 234 can escape through the vent conduit 246 (e.g., as illustrated by arrows 268). Fluid flow and escape through the vent conduit 246 from the interior volume 234 to the exterior 236 can cause the balloon 230 to begin to and continue to deflate (e.g., reducing in size from that shown in FIG. 7 to that shown in FIG. 8).

Figure 9:
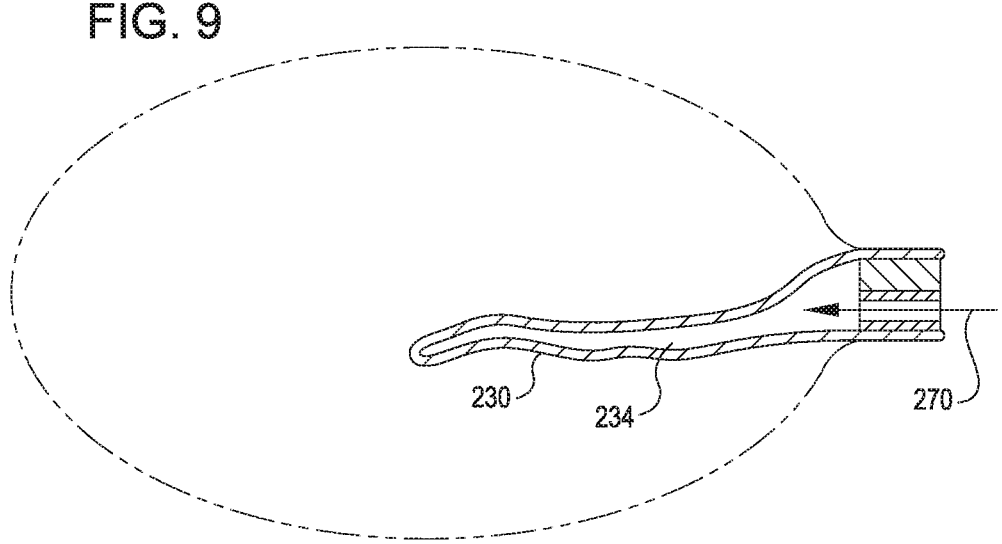
FIG. 9 is a side cutaway view of the intragastric balloon device of FIG. 2 in a fully deflated state ready for passing from the stomach according to certain examples of the present disclosure.

Referring to FIG. 9, fluid flow of the gas out through the vent conduit 246 may continue (e.g., as bubbles into stomach acid liquid) until the balloon 230 is substantially fully deflated. The vent conduit 246 may also permit entry (e.g., as illustrated by arrow 270) of stomach acid into the interior volume 234 of the balloon 230. In some examples, entry of stomach acid can cause the balloon 230 to break apart from the inside out to facilitate passing the remains of the balloon 230 from the stomach 106. In other examples, the balloon 230 may remain intact regardless of entry of stomach acid, yet still be readily passable out of the stomach 106 due to being much smaller in size than when fully inflated (e.g., as shown in solid lines in comparison to the profile of full inflation shown in phantom lines in FIG. 9).

In some examples, other components can be included in the intragastric balloon device 200. For example, features may be included to facilitate tracking of a condition or location of the intragastric balloon device 200 and/or respective components. Non-limiting examples include food coloring or other colorants in the balloon 230 (e.g., in addition to the perfluoropentane or other expanding liquid so that puncture of the balloon 230 can be confirmed by the presence of the color in vomit, excrement, or other bodily fluids), fragrance in the balloon 230 (e.g., so that puncture of the balloon 230 can be confirmed by the presence of the fragrance in burps, flatulence, vomit, excrement, or other bodily expulsions), one or more magnets in the intragastric balloon device 200 (e.g., so that location can be detected via magnetic sensors that may be positioned outside of the body of the patient 102), or electronic transmitter components.

FIG. 10 shows a side cutaway view of a plug 332 that may be utilized in conjunction with a balloon 330 of an intragastric balloon device 300. The plug 332, balloon 330, and intragastric balloon device 300 are respectively examples of the plug 232, balloon 230, and intragastric balloon device 200 described with respect to FIG. 2. In the illustrated embodiment in FIG. 10, the plug 332 includes a plug body 344, a vent conduit 346, a fill conduit 347, and a fuse 348. These features are similar to the features of like names described with respect to FIG. 2, and, as such, descriptions of various aspects of these features are not repeated.

The intragastric balloon device 300 shown in FIG. 10 includes electrical components 372. Although the electrical components 372 are shown in FIG. 10 within the plug 332, in some example, at least some electrical components 372 may be arranged outside of the plug 332 or elsewhere within the intragastric balloon device 200.

In FIG. 10, the electrical components 372 are shown electrically coupled with and supplied by a battery 374. The battery 374 can extract energy from the acid of the stomach 106 to supply power to the electrical components 372. The battery 374 includes an anode 376 and a cathode 378 separated by a permeable membrane 380. When the anode 376, the cathode 378, and membrane 380 are exposed to the stomach acid, a resulting chemical reaction can cause a voltage that can power the electrical components 372.

The battery 374 can be utilized to provide power to any variety of electrical components 372. In some examples, the electrical components 372 permit the intragastric balloon device 300 to be controlled by or otherwise communicate via external energies or signals. As non-limiting examples, the electrical components 372 may respond to magnetic fields, ultrasound signals, or some other applied energies or signals. In some examples, the electrical components 372 can operate according to blue tooth low energy ("BLE") or other communications protocols and associated components. The electrical components 372 may facilitate functions such receiving a control signal, operating a pressure sensor or other type of sensor, sending a signal with data (e.g., to indicate a reading from a sensor or to facilitate location of the intragastric balloon device 200 in the patient), or other functions. For example, the electrical components 372 shown in FIG. 10 include a pressure sensor 382 coupled with a communication component 384 (e.g., which may include a transmitter) so that information about pressure inside the balloon 330 can be transmitted to an external monitoring device. In some examples, the electrical components 372 may receive or generate a deflate command and operate associated components to trigger or accelerate deflation. For example, the electrical components 372 shown in FIG. 10 are coupled with an actuator 386 to cause a piece of nichrome wire or other variety of wire 388 to puncture the balloon 330 (as illustrated by arrow 390) and provide an escape path for deflation in lieu of or in addition to the vent conduit 346. In some examples, the wire 388 may instead be operated to pierce the fuse 348 (as illustrated by arrow 392) or other element associated with the plug 332. In some examples, the actuator 386 may be triggered in response to a pressure reading provided by the pressure sensor 382 and/or in response to a command signal received by the communication component 384 (e.g., which may include a receiver in addition to or in lieu of the transmitter referenced earlier). A movable flap or other obstruction may be associated with the actuator in lieu of the wire 388 and controllable to act as a valve to open a fluid path for deflation.

In the following, further examples are described to facilitate the understanding of the present disclosure.

Example #1

An intragastric balloon device (which may incorporate features of any of the subsequent Examples) comprising a deformable material, wherein the balloon device is in an ingestible form for delivery to a stomach of a patient, expands in response to stimuli in the stomach, and degrades within 72 hours to diminish to passable form in which remains of the intragastric balloon device are passable from the stomach.

Example #2

The intragastric balloon device of Example #1, or any of the preceding or subsequent Examples, wherein the balloon device degrades in less than 36 hours to diminish to passable form.

Example #3

The intragastric balloon device of Example #1, or any of the preceding or subsequent Examples, wherein the balloon device degrades in less than 24 hours to diminish to passable form.

Example #4

The intragastric balloon device of Example #1, or any of the preceding or subsequent Examples, wherein the balloon device degrades in less than 16 hours to diminish to passable form.

Example #5

The intragastric balloon device of Example #1, or any of the preceding or subsequent Examples, wherein the balloon device degrades in less than 12 hours to diminish to passable form.

Example #6

The intragastric balloon device of Example #1, or any of the preceding or subsequent Examples, wherein the balloon device degrades in less than 8 hours to diminish to passable form.

Example #7

The intragastric balloon device of Example #1, or any of the preceding or subsequent Examples, wherein the balloon device degrades in less than 6 hours to diminish to passable form.

Example #8

The intragastric balloon device of Example #1, or any of the preceding or subsequent Examples, wherein the balloon device degrades in less than 4 hours to diminish to passable form.

Example #9

The intragastric balloon device of Example #1, or any of the preceding or subsequent Examples, wherein the balloon device degrades in less than 2 hours to diminish to passable form.

Example #10

The intragastric balloon device of Example #1, or any of the preceding or subsequent Examples, wherein the balloon device further comprises:
  a mouth of the balloon, the mouth defining a transition passage between (i) an interior volume defined and bounded by the deformable material of the balloon, and (ii) an exterior of the balloon;
  a plug disposed in the mouth of the balloon, the plug comprising a vent conduit blocked by a fuse that prevents fluid passage through the vent conduit in the presence of the fuse; and
  a liquid disposed within the interior volume of the balloon and present in a sufficient amount to cause the balloon to inflate as the liquid converts to gas as a temperature of the liquid rises in response to the balloon being located within the body of a patient.

Example #11

The intragastric balloon device of Example #10, or any of the preceding or subsequent Examples, wherein the liquid comprises perfluoropentane.

Example #12

The intragastric balloon device of Example #10, or any of the preceding or subsequent Examples, wherein the fuse comprises methacrylate.

Example #13

The intragastric balloon device of Example #10, or any of the preceding or subsequent Examples, wherein the deformable material of the balloon comprises silicone.

Example #14

The intragastric balloon device of Example #10, or any of the preceding or subsequent Examples, wherein the deformable material of the balloon is coated in parylene.

Example #15

The intragastric balloon device of Example #10, or any of the preceding or subsequent Examples, wherein the intragastric balloon device is encapsulated in a gelatin capsule or other coating that comprises methacrylate or other material that requires an acid environment to degrade to ensure that the capsule will stay intact throughout the esophagus until it reaches the stomach.

Example #16

A method (which may incorporate features of any of the preceding or subsequent Examples) fabricating an ingestible intragastric balloon device, the method comprising:
  providing a balloon comprising a deformable material forming a boundary between an interior volume within the balloon and an exterior outside of the balloon;
  introducing an amount of liquid into the interior volume of the balloon, the amount selected to be sufficient to cause the balloon to inflate as the amount converts from liquid to gas as a temperature of the amount rises in response to the balloon being located within a stomach of a patient; and
  securing a fuse in a position blocking fluid flow through a vent conduit arranged with an interior-facing end in fluid communication with the interior volume and an exterior-facing end in fluid communication with the exterior, wherein characteristics of the fuse are selected to cause the fuse to erode in stomach conditions within 36 hours to a degree that permits fluid passage through the vent conduit to deflate the balloon and facilitate passing of the balloon from the stomach.

Example #17

The method of Example #16, or any of the preceding or subsequent Examples, wherein securing the fuse comprises inserting a plug into a mouth of the balloon, the plug comprising the vent conduit and the fuse.

Example #18

The method of Example #16, or any of the preceding or subsequent Examples, wherein the fuse comprises methacrylate.

Example #19

The method of Example #18, or any of the preceding or subsequent Examples, wherein the fuse formed of a solid mass of methacrylate different from a liquid methacrylate in which a capsule about the balloon is dipped.

Example #20

The method of Example #16, or any of the preceding or subsequent Examples, further comprising:
  encapsulating the balloon having the introduced fluid and secured fuse into a gelatin capsule to convert the balloon into an ingestible form.

Example #21

The method of Example #16, or any of the preceding or subsequent Examples, wherein the introducing the amount of liquid comprises injecting the liquid through a needle extending through a plug received in a mouth of the balloon, and wherein the method further comprises:
  extracting the needle from the plug so that a material of the plug displaces into a space previously occupied by the needle so as to seal against fluid flow through said space.

Example #22

An intragastric balloon device (which may incorporate features of any of the preceding or subsequent Examples) comprising:
  a balloon comprising a deformable material forming a boundary between an interior volume within the balloon and an exterior outside of the balloon;
  perfluoropentane liquid disposed within the interior volume of the balloon and present in a sufficient amount to cause the balloon to inflate toward a predetermined size as the amount of perfluoropentane converts from liquid to gas as a temperature of the perfluoropentane rises in response to the balloon being located within a stomach of a patient;
  a vent conduit having an interior-facing end in fluid communication with the interior volume and an exterior-facing end in communication with the exterior; and
  a fuse comprising methacrylate and disposed blocking fluid flow through the vent conduit, the fuse sized and shaped to erode in stomach conditions within 2-72 hours to a degree that permits fluid passage of the perfluoropentane through the vent conduit to deflate the balloon and facilitate passing of the balloon from the stomach.

Example #23

The intragastric balloon device of Example #22, or any of the preceding or subsequent Examples, further comprising:
  a battery configured to extract energy from stomach acid; and
  an electrical component powered by the battery.

Example #24

The intragastric balloon device of Example #22, or any of the preceding or subsequent Examples, wherein the dissolvable fuse comprises methacrylate cross-linked with a low-pH-soluble material so that the fuse will erode in the stomach in response to contact with stomach acid having a pH below 2.5.

Example #25

A method (which may incorporate features of any of the preceding or subsequent Examples) of suppressing appetite in a subject comprising administering to the subject the intragastric balloon device of Example #1.

Example #26

The method of Example #25, or any of the preceding or subsequent Examples, comprising administering to the subject intragastric balloon devices daily for at least two days.

Example #27

The method of Example #25, or any of the preceding or subsequent Examples, comprising administering to the subject intragastric balloon devices daily for at least one week.

Example #28

The method of Example #25, or any of the preceding or subsequent Examples, comprising administering to the subject intragastric balloon devices daily for at least one month.

Example #29

A method of suppressing appetite in a subject comprising administering to the subject the intragastric balloon device of Example #22, or any of the preceding or subsequent Examples.

Example #30

The method of Example #29, or any of the preceding or subsequent Examples, comprising administering to the subject intragastric balloon devices daily for at least two days.

Example #31

The method of Example #29, or any of the preceding or subsequent Examples, comprising administering to the subject intragastric balloon devices daily for at least one week.

Example #32

The method of Example #29, or any of the preceding Examples, comprising administering to the subject intragastric balloon devices daily for at least one month.

Example #33

The method of Example #29, or any of the preceding Examples, wherein the deformable material of the balloon is degradable over a controlled time in the stomach in order to effect deflation of the balloon and/or passage of the balloon from the stomach.

The foregoing description of some examples has been presented only for the purpose of illustration and description and is not intended to be exhaustive or to limit the disclosure to the precise forms disclosed. Numerous modifications and adaptations thereof will be apparent to those skilled in the art without departing from the spirit and scope of the disclosure. For example, more or fewer steps of the processes described herein may be performed according to the present disclosure. Moreover, other structures may perform one or more steps of the processes described herein.

Reference herein to an example or implementation means that a particular feature, structure, operation, or other characteristic described in connection with the example may be included in at least one implementation of the disclosure. The disclosure is not restricted to the particular examples or implementations described as such. The appearance of the phrases "in one example," "in an example," "in one implementation," or "in an implementation," or variations of the same in various places in the specification does not necessarily refer to the same example or implementation. Any particular feature, structure, operation, or other characteristic described in this specification in relation to one example or implementation may be combined with other features, structures, operations, or other characteristics described in respect of any other example or implementation.

Some examples in this disclosure may include a processor (such as, but not limited to, included in or in communication with the electrical components 372). A computer-readable medium, such as RAM may be coupled to the processor. The processor can execute computer-executable program instructions stored in memory, such as executing one or more computer programs. Such processors may comprise a microprocessor, a digital signal processor (DSP), an application-specific integrated circuit (ASIC), field programmable gate arrays (FPGAs), and state machines. Such processors may further comprise programmable electronic devices, such as programmable logic controllers (PLCs), programmable interrupt controllers (PICs), programmable logic devices (PLDs), programmable read-only memories (PROMs), electronically programmable read-only memories (EPROMs or EEPROMs), or other similar devices.

Such processors may comprise, or may be in communication with, media, for example, computer-readable storage media, that may store instructions that, when executed by the processor, can cause the processor to perform the steps described herein as carried out, or assisted, by a processor. Examples of computer-readable media may include, but are not limited to a memory chip, ROM, RAM, ASIC, or any other medium from which a computer processor can read or write information. The processor, and the processing described, may be in one or more structures, and may be dispersed through one or more structures. The processor may comprise code for carrying out one or more of the methods (or parts of methods) described herein.

Use herein of the word "or" is intended to cover inclusive and exclusive OR conditions. In other words, A or B or C includes any or all of the following alternative combinations as appropriate for a particular usage: A alone; B alone; C alone; A and B only; A and C only; B and C only; and all three of A and B and C.

That which is claimed is:

1. An intragastric balloon device comprising a deformable material, wherein the balloon device is in an ingestible form for delivery to a stomach of a patient, expands in response to stimuli in the stomach, and degrades within 72 hours to diminish to passable form in which remains of the intragastric balloon device are passable from the stomach, wherein the balloon device further comprises:
    a mouth of the balloon, the mouth defining a transition passage between (i) an interior volume defined and bounded by the deformable material of the balloon, and (ii) an exterior of the balloon;
    a plug disposed in the mouth of the balloon, the plug comprising a vent conduit blocked by a fuse that prevents fluid passage through the vent conduit in the presence of the fuse; and
    a liquid disposed within the interior volume of the balloon, sealed within the interior volume by the plug, and present in a sufficient amount to cause the balloon to inflate to a size configured to facilitate a sensation of satiety as the liquid converts to gas as a temperature of the liquid rises in response to the balloon being located within the body of a patient.

2. The intragastric balloon device of claim 1, wherein the balloon device degrades in less than 36 hours to diminish to passable form.

3. The intragastric balloon device of claim 1, wherein the balloon device degrades in less than 24 hours to diminish to passable form.

4. The intragastric balloon device of claim 1, wherein the balloon device degrades in less than 16 hours to diminish to passable form.

5. The intragastric balloon device of claim 1, wherein the balloon device degrades in less than 12 hours to diminish to passable form.

6. The intragastric balloon device of claim 1, wherein the balloon device degrades in less than 8 hours to diminish to passable form.

7. The intragastric balloon device of claim 1, wherein the balloon device degrades in less than 6 hours to diminish to passable form.

8. The intragastric balloon device of claim 1, wherein the balloon device degrades in less than 4 hours to diminish to passable form.

9. The intragastric balloon device of claim 1, wherein the balloon device degrades in less than 2 hours to diminish to passable form.

10. The intragastric balloon device of claim 1, wherein the liquid comprises perfluoropentane.

11. The intragastric balloon device of claim 1, wherein the fuse comprises methacrylate.

12. The intragastric balloon device of claim 1, wherein the deformable material of the balloon comprises silicone.

13. The intragastric balloon device of claim 1, wherein the deformable material of the balloon is coated in parylene.

14. The intragastric balloon device of claim 1, wherein the intragastric balloon device is encapsulated in a gelatin capsule or other coating, wherein the gelatin capsule or other coating comprises methacrylate or other material that requires an acid environment to degrade, and wherein the methacrylate or other material is included to ensure that the gelatin capsule or other coating will stay intact throughout the esophagus until reaching the stomach.

15. A method of fabricating an ingestible intragastric balloon device, the method comprising:
   providing a balloon comprising a deformable material forming a boundary between an interior volume within the balloon and an exterior outside of the balloon;
   introducing an amount of liquid into the interior volume of the balloon, the amount selected to be sufficient to cause the balloon to inflate to a size configured to facilitate a sensation of satiety as the amount converts from liquid to gas as a temperature of the amount rises in response to the balloon being located within a stomach of a patient; and
   securing a fuse in a position blocking fluid flow through a vent conduit arranged with an interior-facing end in fluid communication with the interior volume and an exterior-facing end in fluid communication with the exterior, wherein the liquid is sealed within the interior volume by the presence of the fuse, and wherein characteristics of the fuse are selected to cause the fuse to erode in stomach conditions within 72 hours to a degree that permits fluid passage through the vent conduit to deflate the balloon and facilitate passing of the balloon from the stomach.

16. The method of claim 15, wherein securing the fuse comprises inserting a plug into a mouth of the balloon, the plug comprising the vent conduit and the fuse.

17. The method of claim 15, wherein the fuse comprises methacrylate.

18. The method of claim 17, further comprising:
   enclosing the device within a capsule; and
   dipping the capsule into a liquid methacrylate coating, wherein the fuse is formed of a solid mass of methacrylate having a different concentration from the liquid methacrylate coating.

19. The method of claim 15, further comprising:
   encapsulating the balloon having the introduced fluid and secured fuse into a gelatin capsule to convert the balloon into an ingestible form.

20. The method of claim 15, wherein the introducing the amount of liquid comprises injecting the liquid through a needle extending through a plug received in a mouth of the balloon, and wherein the method further comprises:
   extracting the needle from the plug so that a material of the plug displaces into a space previously occupied by the needle so as to seal against fluid flow through said space.

21. An intragastric balloon device comprising:
   a balloon comprising a deformable material forming a boundary between an interior volume within the balloon and an exterior outside of the balloon;
   a plug disposed as a barrier between the interior volume and the exterior;
   perfluoropentane liquid disposed within the interior volume of the balloon, sealed within the interior volume by the plug, and present in a sufficient amount to cause the balloon to inflate to a predetermined size configured to facilitate a sensation of satiety as the amount of perfluoropentane converts from liquid to gas as a temperature of the perfluoropentane rises in response to the balloon being located within a stomach of a patient;
   a vent conduit disposed in the plug and having an interior-facing end in fluid communication with the interior volume and an exterior-facing end in communication with the exterior; and
   a fuse comprising methacrylate and disposed blocking fluid flow through the vent conduit, the fuse sized and shaped to erode in stomach conditions within 2-72 hours to a degree that permits fluid passage of the perfluoropentane through the vent conduit to deflate the balloon and facilitate passing of the balloon from the stomach.

22. The intragastric balloon device of claim 21, further comprising:
   a battery configured to extract energy from stomach acid; and
   an electrical component powered by the battery.

23. The intragastric balloon device of claim 21, wherein the dissolvable fuse comprises methacrylate cross-linked with a low-pH-soluble material so that the fuse will erode in the stomach in response to contact with stomach acid having a pH below 2.5.

24. A method of suppressing appetite in a subject comprising administering to the subject the intragastric balloon device of claim 1.

25. The method of claim 24 comprising administering to the subject intragastric balloon devices daily for at least two days.

26. The method of claim 24 comprising administering to the subject intragastric balloon devices daily for at least one week.

27. The method of claim 24 comprising administering to the subject intragastric balloon devices daily for at least one month.

28. A method of suppressing appetite in a subject comprising administering to the subject the intragastric balloon device of claim 21.

29. The method of claim 28 comprising administering to the subject intragastric balloon devices daily for at least two days.

30. The method of claim 28 comprising administering to the subject intragastric balloon devices daily for at least one week.

31. The method of claim 28 comprising administering to the subject intragastric balloon devices daily for at least one month.

32. The method of claim 28, wherein the deformable material of the balloon is degradable over a controlled time in the stomach in order to effect deflation of the balloon and/or passage of the balloon from the stomach.

* * * * *